(12) United States Patent
Freedman

(10) Patent No.: US 8,076,933 B2
(45) Date of Patent: Dec. 13, 2011

(54) METHOD FOR DETERMINING WETTABILITY OF AN OIL RESERVOIR

(75) Inventor: Robert Freedman, Houston, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 248 days.

(21) Appl. No.: 12/431,847

(22) Filed: Apr. 29, 2009

(65) Prior Publication Data

US 2010/0277165 A1    Nov. 4, 2010

(51) Int. Cl.
*G01V 3/00* (2006.01)
(52) U.S. Cl. .................................... 324/303
(58) Field of Classification Search .......... 324/300–322
See application file for complete search history.

(56) References Cited

U.S. PATENT DOCUMENTS

| | | | |
|---|---|---|---|
| 3,657,730 A | 4/1972 | Robinson et al. | |
| 5,023,551 A | 6/1991 | Kleinberg et al. | |
| 5,055,787 A | 10/1991 | Kleinberg et al. | |
| 5,162,733 A * | 11/1992 | Baldwin | 324/307 |
| 5,578,922 A | 11/1996 | Lurie et al. | |
| 6,229,308 B1 | 5/2001 | Freedman | |
| 6,346,813 B1 | 2/2002 | Kleinberg | |
| 6,765,380 B2 * | 7/2004 | Freedman et al. | 324/303 |
| 6,883,702 B2 * | 4/2005 | Hurlimann et al. | 324/303 |
| 7,397,240 B2 | 7/2008 | Fleury et al. | |

OTHER PUBLICATIONS

Freedman, R. et al., Wettability, Saturation, and viscosity Using the Magnetic Resonance Fluid Characterization Method and New Diffusion-Editing Pulse Sequences, SPE 77397, Sep. 29-Oct. 2, 2002.
DePavia, L. et al., A Next-Generation Wireline NMR Logging Tool, SPE 84482, Oct. 5-8, 2003.

* cited by examiner

*Primary Examiner* — Dixomara Vargas
(74) *Attorney, Agent, or Firm* — David J. Smith

(57) ABSTRACT

A method for determining wettability of an earth formation zone surrounding a borehole, including the following steps: introducing paramagnetic ions into the water component of the zone; performing NMR measurements on the zone, and determining an NMR relaxation time parameter for the zone; extracting a fluid sample from the zone; performing NMR measurements on the sample, and determining the NMR relaxation time parameter for the sample; and determining wettability of the earth formation zone using the determined relaxation time parameter for the zone and the determined relaxation time parameter for the sample.

20 Claims, 5 Drawing Sheets

US 8,076,933 B2

METHOD FOR DETERMINING WETTABILITY OF AN OIL RESERVOIR

FIELD OF THE INVENTION

This invention relates to the field of well logging and, more particularly to a method for determining wettability of an earth formation zone surrounding a borehole.

BACKGROUND OF THE INVENTION

Background description of wettability is presented, for example, in Freedman et al., SPE Paper 77397, present at the 2002 meeting of Society of Petroleum Engineers. As described therein, wettability is the tendency of a fluid to spread on and preferentially adhere to or "wet" a solid surface in the presence of other immiscible fluids. Knowledge of reservoir wettability is critical because it influences important reservoir properties including residual oil saturation, relative permeability, and capillary pressure. An understanding of the wettability of a reservoir is crucial for determining the most efficient means of oil recovery. This is becoming increasingly important as more secondary and tertiary recovery projects are being undertaken to recover remaining reserves after primary production. It is generally believed that most reservoirs are water wet or mixed wet. In mixed-wet rocks the brine phase occupies the smaller pores, which are therefore water wet. In the larger oil- and brine-filled pores the oil wets part of the pore surfaces.

Two widely used laboratory indicators of wettability are contact angles measured in water-oil-solid systems and the Amott wettability index. A practical limitation of contact angle measurements is that they are restricted to special geometries and cannot be made on reservoir rocks. The Amott wettability index is determined from the amount of oil displaced from a core, starting at some initial oil saturation, by spontaneous imbibition of brine divided by the amount of oil displaced by both spontaneous and forced imbibition. Amott defines an analogous index by also considering the displacement of water by oil. The Amott indices vary linearly on a scale from 0 to 1. The endpoints for the displacement of oil by water are 0 for a neutral to oil-wet system and 1 for a strongly water-wet system. Imbibition measurements like the Amott index provide the most quantitative indicators of wettability, but they are limited to the laboratory.

NMR measurements on fluid-saturated porous media are sensitive to wettability because of the enhanced relaxation rate caused when fluid molecules come into contact with pore surfaces that contain paramagnetic ions or magnetic impurities. Surface relaxation of nuclear magnetism is usually the dominant relaxation mechanism for the wetting phase in a partially saturated rock. The nonwetting phase is unaffected by surface relaxation because the pore surface is coated by the wetting fluid. The other relaxation mechanisms, bulk and diffusion relaxation, affect both the wetting and nonwetting phases. The relaxation rate of the transverse magnetization measured in a spin-echo experiment is the sum of the relaxation rates from all three mechanisms. The bulk relaxation rates for liquids are proportional to their viscosities.

Freedman et al. U.S. Pat. No. 6,765,380, assigned to the same assignee as the present application, had pointed out that many laboratory NMR wettability studies have been reported in the literature, but that reservoir wettability determination from laboratory measurements is not definitive because it is not possible to accurately mimic reservoir conditions in the laboratory. In fact, the very processes required to obtain laboratory samples can alter the reservoir wettability.

The referenced '380 patent disclosed a method for determining reservoir wettability under downhole conditions. The technique thereof involved using an NMR logging tool to acquire a first set of NMR measurements of formation fluids in earth formations at a selected axial depth and inverting the first set of the NMR measurements to produce a first distribution of a spin relaxation parameter for a fluid component in the formation fluids. A formation fluid testing tool is used to obtain a formation fluid sample, and a second set of NMR measurements are made on the fluid sample. The second set of NMR measurement is inverted to produce a second distribution of the spin relaxation parameter for the fluid component in the formation fluid sample.

As described further in the '380 patent, the method thereof involves joint interpretation of diffusion measurements made by conventional NMR logging tools and NMR measurements made in the flowline of a fluid sampling tool. The diffusion measurements are used to separate the NMR oil and water signals from the fluids contained in the rock pore spaces. The conventional NMR tool diffusion measurements are inverted in the method of the '380 patent to compute separate oil and water relaxation time distributions. As described therein, the inversion can be performed using the technique disclosed in Freedman U.S. Pat. No. 6,229,308, the technique being known as the "magnetic resonance fluid characterization method" or "MRF method". As described in the '308 patent, the MRF method is a diffusion-based inversion that requires accurate knowledge of the magnetic field gradient in the pore spaces of the rock investigated by the NMR tool.

The computation of T1 and T2 distributions of reservoir oil contained in reservoir rock is fundamental to the '380 patent. The diffusion method for computing oil relaxation time distributions in the pore spaces of reservoir rocks can be problematic if the NMR magnet induces internal magnetic gradients in the rock. In this case the magnetic field gradients in the pore spaces are not known and the diffusion method employed in the '380 patent has limitations in computing accurate water and oil relaxation time distributions. Induced internal gradients are commonly encountered in sandstone formations because of the presence of iron and/or other magnetic minerals. For example, iron is present in chlorite, a clay mineral commonly found in sandstone rocks. Because of induced gradients, the method of the '380 patent may not always be reliable in sandstone formations. Another limitation of the diffusion method used in the '380 patent occurs when the reservoir oil and water have nearly identical diffusion coefficients and overlapping relaxation time distributions.

It is among the objectives of the present invention to overcome problems and limitations of prior art techniques, including those summarized above.

SUMMARY OF THE INVENTION

An advantage of the technique of the present invention is that it can be used to determine wettability without relying on diffusion, and is therefore not substantially affected by magnetic field gradients. Moreover, the method hereof does not rely on the oil and water in the reservoir having a contrast in diffusion coefficients or relaxation times in order to determine accurate oil relaxation time distributions in the reservoir rock.

In accordance with an embodiment of the invention, a method is set forth for determining wettability of an earth formation zone surrounding a borehole, comprising the following steps: introducing paramagnetic ions into the water component of the zone; performing NMR measurements on the zone, and determining an NMR relaxation time parameter for the zone; extracting a fluid sample from the zone; performing NMR measurements on the sample, and determining said NMR relaxation time parameter for the sample; and determining wettability of the earth formation zone using the determined relaxation time parameter for the zone and the determined relaxation time parameter for the sample.

In a preferred embodiment of the invention, the step of introducing paramagnetic ions into the water component of the zone comprises injecting a solution of paramagnetic ions into the zone to substantially replace water in the zone. In this embodiment, the step of determining wettability of the earth formation zone using the determined relaxation time parameter for the zone and the determined relaxation time parameter for the sample includes comparing an oil component of said determined relaxation time parameter for the zone with an oil component of said determined relaxation time parameter for the sample.

In a preferred embodiment of the invention, the relaxation time parameter comprises the distribution of the oil component of the longitudinal relaxation times, $T_1$. In this embodiment, the step of performing the NMR measurements on the earth formation zone preferably includes making longitudinal relaxation time measurements on the zone, and said determining of an NMR relaxation time parameter comprises determining a distribution of said longitudinal relaxation time measurements. Alternatively, although with more complexity, the relaxation time parameter comprises the distribution of transverse relaxation times, $T_2$, corrected for the gradient of the static magnetic field used in performing the NMR measurements.

Further features and advantages of the invention will become more readily apparent from the following detailed description when taken in conjunction with the accompanying drawings.

DETAILED DESCRIPTION

Figure 1:
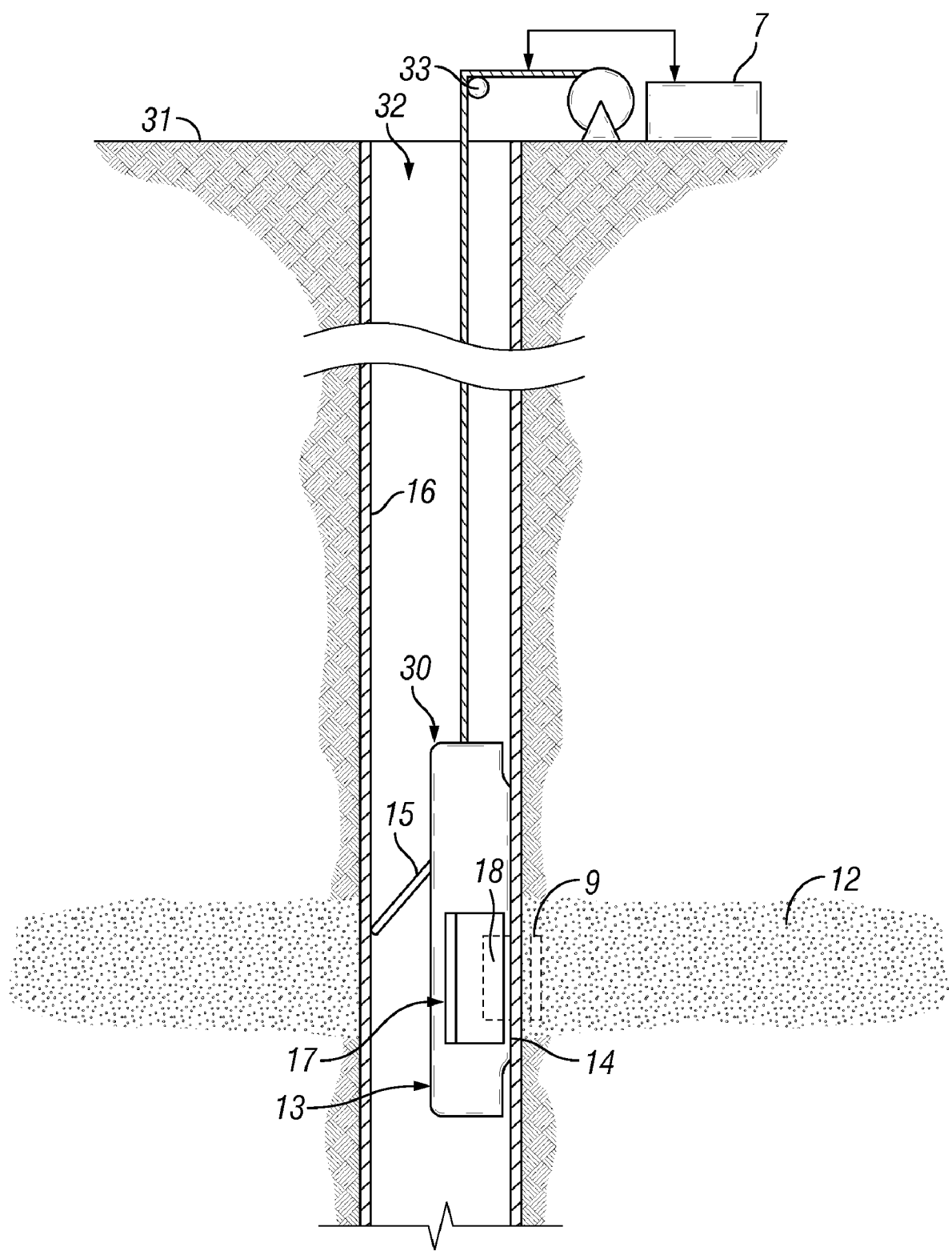
FIG. 1 is a diagram, partially in block form, of a well logging apparatus which can be used in practicing embodiments of the invention.

Referring to FIG. 1, there is shown an apparatus for investigating subsurface formations 31 traversed by a borehole 32, which can be one of the equipments used in practicing embodiments of the invention. Reference can be made, for example, to U.S. Pat. No. 5,055,787. The borehole 32 is typically filled with a drilling fluid or mud which contains finely divided solids in suspension, and mudcake 16 is shown on the walls of the borehole. The preferred operation of the invention is in a borehole drilled with water based mud.

A magnetic resonance investigating apparatus or logging device 30 is suspended in the borehole 32 on an armored cable 33, the length of which substantially determines the relative depth of the device 30. The length of cable 33 is controlled by suitable means at the surface such as a drum and winch mechanism (not shown). Surface equipment, represented at 7, can be of conventional type, and can include a processor subsystem which includes a recorder and other peripherals, and which communicates with the all the downhole equipment. It will be understood that at least part of the processing can be performed downhole and/or uphole, and that some of the processing may, if desired, be performed at a remote location. Also, while a wireline is illustrated, alternative forms of physical support and communicating link can be used, for example in a measurement while drilling system. As described for example in the U.S. Pat. No. 5,055,787, the magnetic resonance logging device 30 has a face 14 shaped to intimately contact the borehole wall, with minimal gaps or standoff, and a retractable arm 15 which can be activated to press the body of the tool 13 against the borehole wall during a logging run, with the face 14 pressed against the wall's surface. Although the tool 13 is shown as a single body, the tool may alternatively comprise separate components such as a cartridge, sonde or skid, and the tool may be combinable with other logging and/or testing tools.

The magnetic resonance logging device 30 includes a magnet array 17 and an RF antenna 18 positioned between the array 17 and the wall engaging face 14. Magnet array 17 produces a static magnetic field $B_0$ in regions surrounding the tool 13. The antenna 18 produces, at selected times, an oscillating magnetic field $B_1$ which is focused into formation 12, and is superposed on the static field $B_0$ within those parts of formation opposite the face 14. The typical "volume of investigation" or zone of the tool, shown in dashed region 9 in FIG. 11, is a vertically elongated region directly in front of tool face 14. Reference can also be made to Morriss, C. E., Deutch, P., Freedman, R., McKeon, D., Kleinberg, R. L., 1996, "Operating Guide for the Combinable Magnetic Resonance Tool", Log Analyst, November-December 1996, pg. 53-60.

Figure 2:
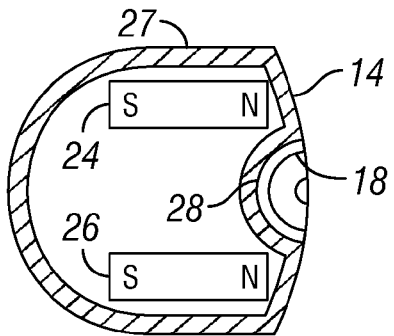
FIG. 2 is a cross-sectional diagram of a portion of the nuclear magnetic resonance logging device of FIG. 1.

FIG. 2 shows a magnet array 17 of the type disclosed in the referenced '787 patent. The magnet array includes two permanent magnets 24 and 26, which are mounted generally parallel to each other within a metal alloy body 27. The body 27 should be of a material having low magnetic permeability, so as to not interfere with the static magnetic field. Magnets 24 and 26 are slabs which are elongated in the longitudinal direction of the borehole. The magnetic poles of each magnet are not on the smallest faces of the slab, commonly viewed as the ends of a bar magnet. Instead, the poles appear on the two opposing edges of the slab magnet and point to the left and right, respectively, in the Figure. Therefore, within the formation 12, the magnetic field $B_0$ surrounding the magnets remains fairly constant along the longitudinal direction of the borehole axis. In the illustration of FIG. 2, magnets 24, 26 are symmetrically mounted in the two sides of the body 27 with the north poles facing the same direction, that is, the direction of the face 14 of the tool. One or more further permanent magnets can be used.

Figure 3:
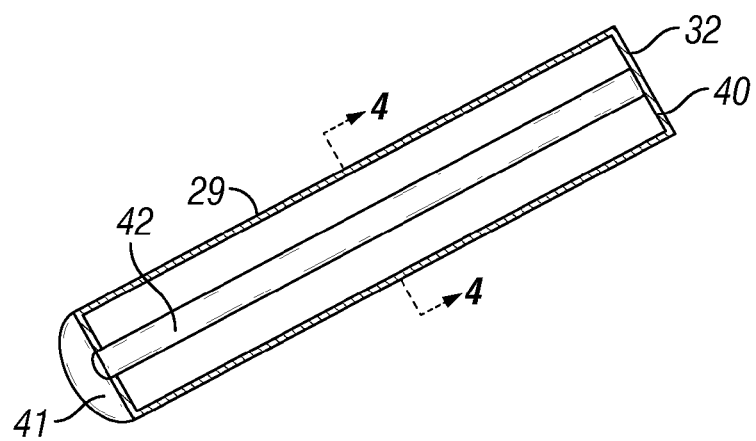
FIG. 3 is a perspective view of the RF antenna of the FIG. 1 nuclear magnetic resonance logging device.
Figure 4:
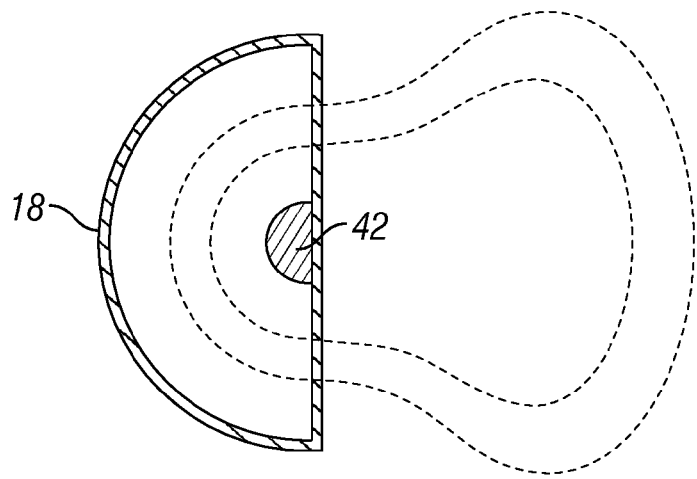
FIG. 4 is a cross-sectional view of the RF antenna of FIG. 3 as taken through a section defined by the arrows 4-4 in FIG. 3.

As also described in the referenced '787 patent, the metal body 27 has, on the front face 14 thereof, a semi-cylindrically shaped cavity or slot 28 which faces formations engaged by the face 14. The cavity 28 is adapted for receiving an RF antenna 18 that is shown in FIGS. 3 and 4. The antenna 18 is positioned outside of the metal body 27 (FIG. 2) of the tool, and is thereby shielded from electromagnetic communication with regions of the borehole which lie behind the body 27, or regions of other formations in directions intercepted by the body 27. Antenna 18 is thus responsive only to magnetic fields originating in front of the wall engaging face 14.

In the referenced '787 patent, the antenna 18 is used both as an RF transmitter to produce an oscillating magnetic field in the formations, and as a receiving antenna to detect magnetic signals. The antenna, which has a body 29 and an elongated center probe 42, across which signals are applied and detected, serves effectively as a current loop which produces an oscillating magnetic field $B_1$ within the volume of investigation that is perpendicular to the static magnetic field, $B_0$ (which is radial in the volume of investigation). The body 29 is trough-shaped and has end plates 40, 41 with the center conductor or probe 42 extending from one end plate 40 to the other end plate 41, parallel to and centered in the semi-cylindrical trough 29.

It is known in the art that an NMR logging device can be capable of performing measurements at plural depths of investigation. An example of an NMR logging device that has plural depths of investigation is the "MRX" (trademark of Schlumberger) disclosed, for example, in L. DePavia et al., "A Next-Generation Wireline NMR Logging Tool" Society of Petroleum Engineers, SPE 84482, 2003. As described in that publication, the "MRX" tool has multiple frequencies of operation corresponding to independent measurement volumes (shells) with evenly spaced depths of investigation. This capability can be utilized, inter alia, for making diffusion measurements. Although any suitable NMR logging tool can be used in making formation measurements used in the present invention, an advantage of the invention is that diffusion measurements are not required, so less complex equipment and measurements can be utilized, with attendant advantage in cost and logging speed.

Figure 5:
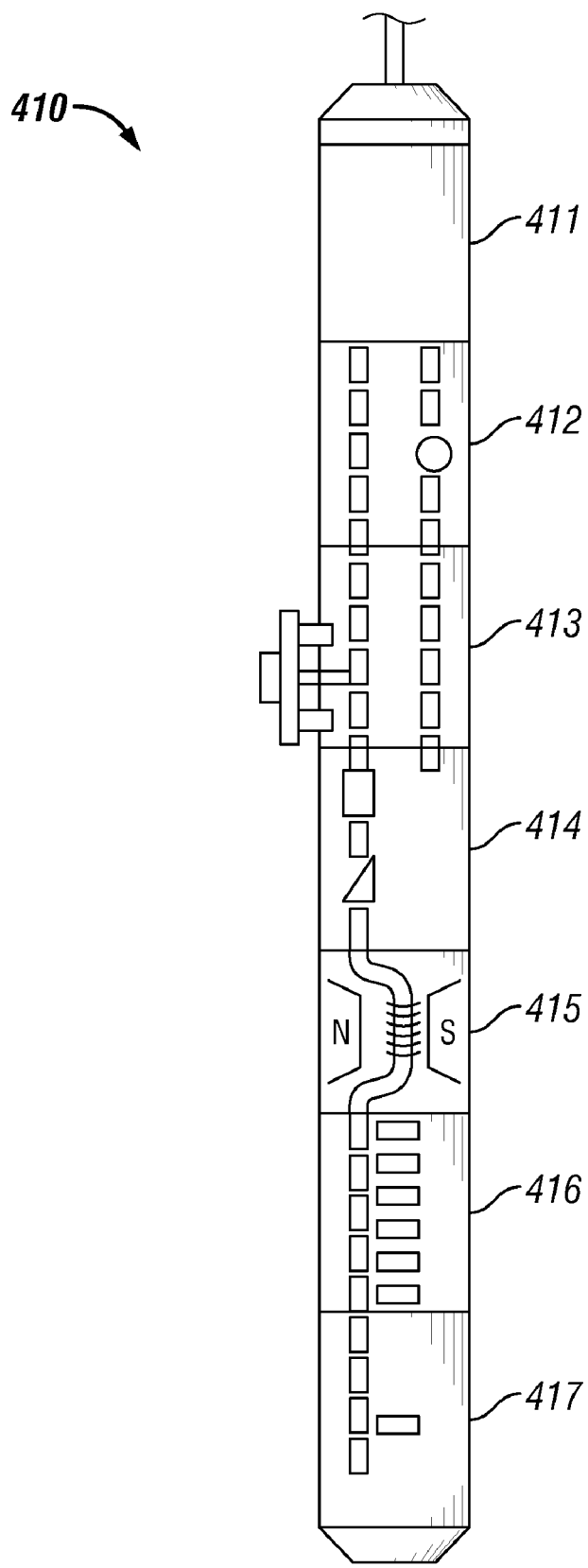
FIG. 5 is a schematic diagram partially in block form, of a fluid sampling tool utilized for extracting and measuring formation fluid which can be used in practicing an embodiment of the invention.

A type of equipment for extracting formation fluids and making NMR measurements thereon, which is an example of another equipment that can be used in practicing embodiments of the invention, is disclosed in U.S. Pat. No. 6,346,813. FIG. 5 shows a formation fluid testing (or sampling) tool 410 that is described in the '813 patent and includes the following modules: an electronic module 411, which may include a processor and a memory; a hydraulic power module 412; a probe module 413, which may be deployed to make a hydraulic seal with the formation; a pumpout module 417; an optical fluid analyzer (OFA) 414; an NMR module 415, and a multisample module 416. As before, the logging tool 410 can be suspended in an earth borehole on an armored multiconductor cable, the length of which substantially determines the depth of the tool, and equipment at the earth's surface can include control and communication circuitry for the logging apparatus. A was first shown in FIG. 1, the surface equipment can typically include a processor and a recorder. Although the control and processing associated with embodiments hereof may be performed by downhole and uphole processors, it will be understood that parts of the processing may be performed at locations remote from the borehole, which may be in direct or indirect communication with the wellsite. Also, as previously noted, while embodiments hereof are described in the context of wireline logging equipment, it will be understood that the invention can also have application to logging while drilling, tripping, and/or pausing, or other investigation in an earth borehole.

Figure 6:
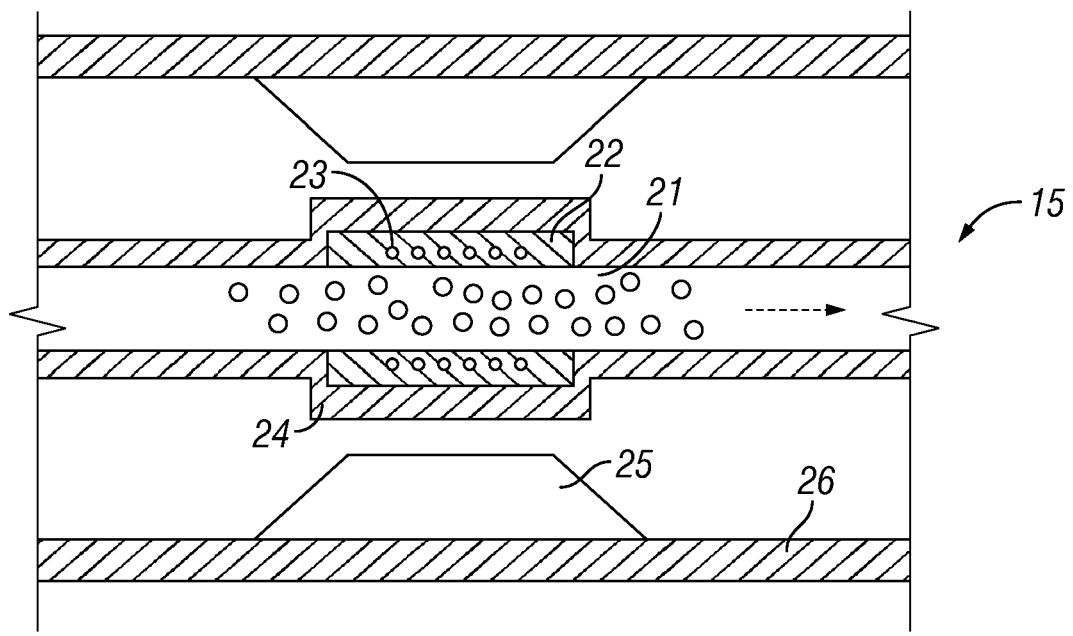
FIG. 6 shows a schematic axial section of a flow line NMR apparatus which is part of the sampling tool of FIG. 5.

The NMR module 415 of the tool, used for an embodiment hereof, is shown in FIG. 6. Fluid withdrawn from the formation flows through a flow channel 21. In non-instrumented sections of the tool, the channel is defined by a thick-wall metal tube 24 capable of withstanding formation pressure. The channel is defined by the inside diameter of an antenna support 22. The antenna support is made of a non-conductive and nonmagnetic material. The NMR antenna 23 is embedded in the antenna support. The NMR antenna, such as a solenoid, radiates a magnetic field. The antenna support is enclosed by an enlarged portion of thick-wall metal tube 24, so as not to obstruct the flow channel 21. The tube 24 and antenna support 22 are able to contain the high pressure formation fluids in the flow channel. An array of permanent magnets 25 is placed outside the thick-wall metal tube. These create a constant magnetic field, substantially perpendicular to the field generated by the antenna. The entire NMR apparatus is enclosed in a sonde housing 26 which is attached to other similar housings in the tool string lowered into the well. Although FIGS. 5 and 6 illustrate an arrangement involving measurements on fluid in a flowline, it will be understood that the NMR equipment can be employed, for example, in an auxiliary or bypass line of a formation fluid testing tool.

Figure 7:
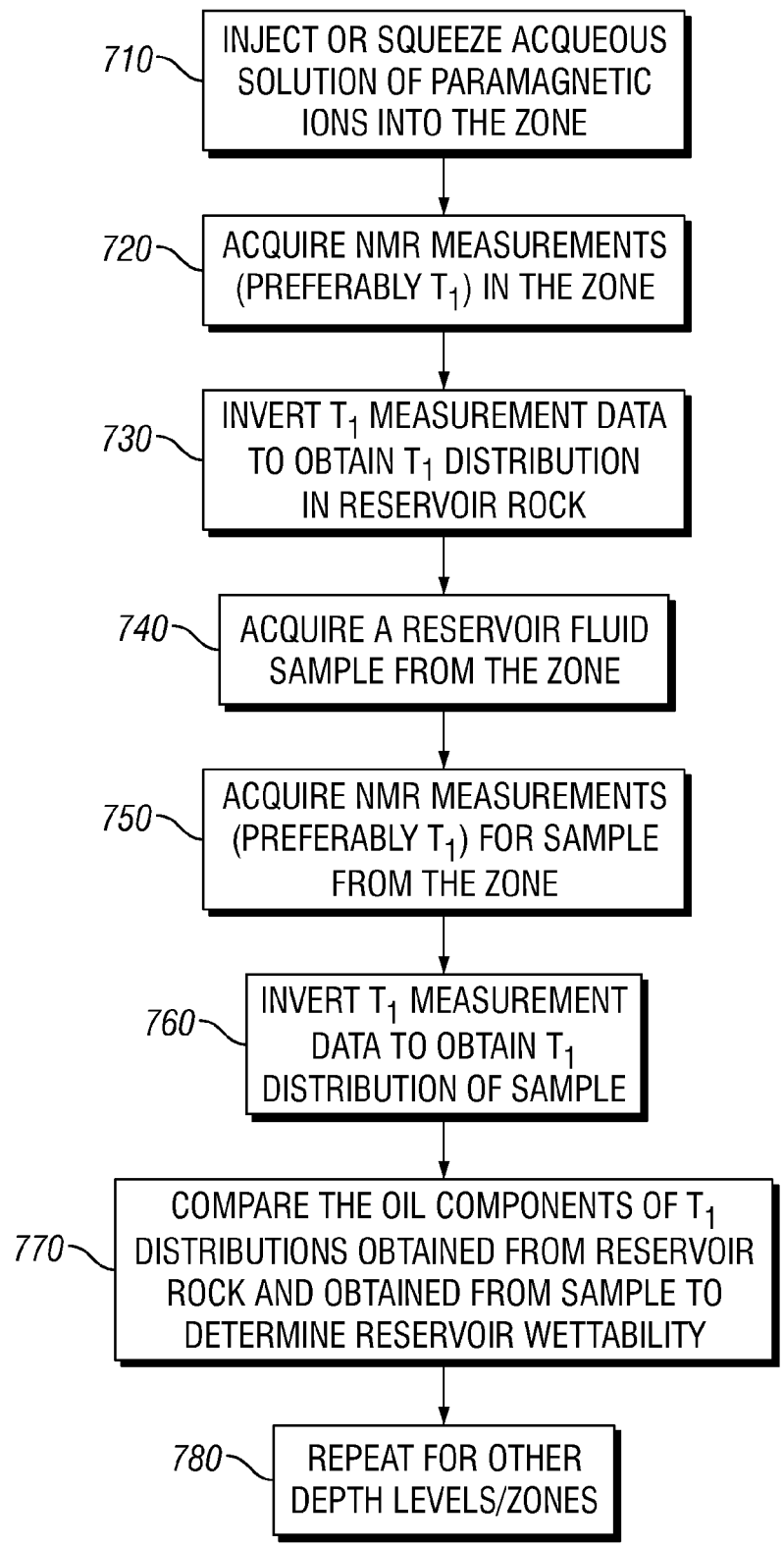
FIG. 7 is a flow diagram for implementing the steps of an embodiment of the invention.

FIG. 7 is a flow diagram of steps of a method, including control of downhole and uphole processors, in accordance with an embodiment of the invention. The block 710 represents the introducing of paramagnetic ions into a selected depth interval of the formations, including the zone of investigation. This can be done by injecting or squeezing an aqueous solution of the paramagnetic ions into at least the selected depth intervals, using a known technique, such as that disclosed in the U.S. Pat. No. 3,657,730. As disclosed therein, an aqueous paramagnetic solution of chelated Mn-EDTA (ethylene-diamine-tetra-acetic acid) can be used to reduce the T1 of the brine phase to about 15 milliseconds. The solution is injected into the formation to displace the formation brine in the zone of investigation of the NMR tool. As also disclosed in the '730 patent, an inflatable packer can be utilized to define the approximate extent of the treated depth interval, and the desired solution can be pumped in through the drill string. It will be understood, however, that any suitable technique for introduction of the paramagnetic ions can be utilized. See, for example, Horkowitz et al. (Paper Q, presented at the SPWLA Annual Logging Symposium, Jun. 26-29, 1995) which reviews procedures for injecting chelated Mn-EDTA solution into a formation and discusses the use of an aqueous paramagnetic solution of $MnCl_2$ to measure residual oil saturation in a carbonate formation. The $MnCl_2$ is a less expensive; however, the Mn-EDTA is preferred in sandstone formations because it is more stable in the presence of clays. It will be understood that other suitable materials can also be employed.

The block 720 represents the acquiring of the NMR relaxation time measurements over the selected depth interval or zone. In the preferred embodiment, this measurement will include obtaining the relaxation time data using, for example, the type of equipment described above in conjunction with FIGS. 1-4. Preferably, the longitudinal relaxation times ($T_1$) are measured using a known technique, for example a "saturation recovery" (sometimes referred to as "variable wait time") or an "inversion recovery" pulse sequence. Reference can be made, for example, to U.S. Pat. No. 5,023,551. The oil phase relaxation times are unaffected by the paramagnetic ions because of the immiscibility of the oil and aqueous phases. (If it is desired to measure transverse relaxation time, $T_2$, a Carr-Purcell-Meiboom-Gill pulse sequence or other suitable pulse sequence can be employed, although magnetic field gradients can affect the measurements and may need to be corrected for. Also, if desired, a so-called "T1-CPMG" can be applied for determination both $T_1$ and $T_2$ distributions in a subsequent two-dimensional inversion.) Then, as represented by the block 730, the $T_1$ measurement data is inverted to determine the $T_1$ distribution in the reservoir rock of the zone. Because of the insertion of the paramagnetic ions, the longitudinal relaxation time distribution of the water component will peak at a very fast time, so the oil peak will typically be relatively distinct and unambiguous.

The block 740 represents acquisition of a reservoir fluid sample from the selected depth interval or zone, and the block 750 represents the acquiring of NMR relaxation time measurements for the sample. In an embodiment hereof, these steps can be performed using the formation testing tool of FIG. 5 and the NMR module of FIG. 6, as previously described. Again, longitudinal relaxation time ($T_1$) data is preferably acquired, using, for example, a saturation recovery or inversion recovery pulse sequence.

Next, the block 760 represents inversion of the measurement data (as indicated, preferably $T_1$) from the sample to compute the relaxation time distribution for the bulk crude oil. Then, the block 770 represents comparing of the oil component of the relaxation time distribution (again, preferably the $T_1$ distribution) determined for the reservoir rock zone and the oil component of the corresponding relaxation time distribution determined for the sample, in order to determine the reservoir wettability for the zone.

The block 780 represents repeating the procedure for other depth levels and/or zones, and forming a log of wettability, for example as a function of depth level.

The invention has been described with reference to particular preferred embodiments, but variations within the spirit and scope of the invention will occur to those skilled in the art. For example, it will be understood that the order of performing some of the measurement and inversion steps can be modified. Also, the fluid sample can, if desired, be brought to the surface for measurement and analysis.

The invention claimed is:

1. A method for determining wettability of an earth formation zone surrounding a borehole, comprising the steps of:
   introducing paramagnetic ions into the water component of said zone;
   performing NMR measurements on said zone, and determining an NMR relaxation time parameter for said zone;
   extracting a fluid sample from said zone;
   performing NMR measurements on said sample, and determining said NMR relaxation time parameter for said sample; and
   determining wettability of said earth formation zone using said determined relaxation time parameter for said zone and said determined relaxation time parameter for said sample.

2. The method as defined by claim 1, wherein said step of introducing paramagnetic ions into the water component of said zone comprises injecting a solution of paramagnetic ions into said zone to substantially replace water in said zone.

3. The method as defined by claim 1, wherein said step of determining wettability of said earth formation zone using said determined relaxation time parameter for said zone and said determined relaxation time parameter for said sample includes comparing an oil component of said determined relaxation time parameter for said zone with an oil component of said determined relaxation time parameter for said sample.

4. The method as defined by claim 1, wherein said relaxation time parameter comprises the distribution of longitudinal relaxation times, T1.

5. The method as defined by claim 1, wherein said relaxation time parameter comprises the distribution of the oil component of the longitudinal relaxation times, T1.

6. The method as defined by claim 3, wherein said relaxation time parameter comprises the distribution of the oil component of the longitudinal relaxation times, T1.

7. The method as defined by claim 1, wherein said relaxation time parameter comprises the distribution of transverse relaxation times, T2, corrected for the gradient of the static magnetic field used in performing the NMR measurements.

8. The method as defined by claim 1, wherein said step of performing said NMR measurements on said earth formation zone includes making longitudinal relaxation time measurements on said zone, and said determining of an NMR relaxation time parameter comprises determining a distribution of said longitudinal relaxation time measurements.

9. The method as defined by claim 1, wherein said step of performing NMR measurements on said earth formation zone is performed with a logging device that is movable through the borehole on a wireline.

10. The method as defined by claim 1, wherein said step of performing NMR measurements on said earth formation zone is performed with a logging device that is movable through the borehole on a drillstring.

11. The method as defined by claim 1, wherein said step of extracting a fluid sample from said zone is performed with a formation testing device that is movable through the borehole on a wireline.

12. The method as defined by claim 1, wherein said step of extracting a fluid sample from said zone is performed with a formation testing device that is movable through the borehole on a drillstring.

13. The method as defined by claim 1, wherein said steps of performing NMR measurements on said zone and extracting a fluid sample from said zone are performed in any desired order.

14. The method as defined by claim 1, wherein said step of determining an NMR relaxation parameter for said zone is performed at least partially downhole.

15. The method as defined by claim 1, wherein said step of determining an NMR relaxation parameter for said zone is performed at least partially uphole.

16. The method as defined by claim 1, wherein said step of performing NMR measurements on said sample and determining said NMR measurements on said sample and determining said NMR relaxation parameter for said sample is performed at least partially downhole.

17. The method as defined by claim 1, wherein said step of performing NMR measurements on said sample and determining said NMR measurements on said sample and determining said NMR relaxation parameter for said sample is performed at least partially uphole.

18. The method as defined by claim 1, further comprising repeating all the recited steps for other earth formation zones.

19. The method as defined by claim 1, further comprising repeating all the recited steps for zones at other borehole depths in the formations, and producing a log of wettability as a function of borehole depth.

20. A method for determining wettability of an earth formation zone surrounding a borehole, comprising the steps of:
   injecting paramagnetic ions into a water component of the formation zone to replace at least a portion the water component in the formation zone;
   performing NMR measurements on the formation, and determining an NMR relaxation time parameter for said zone;
   extracting a fluid sample the formation zone;
   performing NMR measurements on the fluid sample, and determining said NMR relaxation time parameter for the fluid sample; and
   determining wettability of the formation using the determined relaxation time parameter for the formation zone and the determined relaxation time parameter for the fluid sample without use of diffusion measurements.

* * * * *